(12) United States Patent
Matsui et al.

(10) Patent No.: US 6,339,172 B1
(45) Date of Patent: Jan. 15, 2002

(54) ASSAY OF SUBSTANCE IN BIOLOGICAL SAMPLE USING LABELED PROBE

(75) Inventors: Kazuhiro Matsui; Katsunori Ikeda, both of Tsuruga; Shinichi Teshima, Osaka; Yoshihisa Kawamura, Tsuruga; Kazuko Matsumoto, 2578-1-708, Noborito, Tama-ku, Kawasaki-shi, Kanagawa 214-0014, all of (JP)

(73) Assignees: Kazuko Matsumoto, Kawasa; Toyo Boseki Kabushiki Kaisha, Osaka, both of (JP)

( * ) Notice: Subject to any disclaimer, the term of this patent is extended or adjusted under 35 U.S.C. 154(b) by 0 days.

(21) Appl. No.: 09/301,406

(22) Filed: Apr. 28, 1999

(30) Foreign Application Priority Data

Apr. 28, 1998 (JP) ............................................ 10-119768
Jun. 30, 1998 (JP) ............................................ 10-184852

(51) Int. Cl.$^7$ .................... C07C 309/00; C07D 333/74; C07D 333/56; C12Q 1/70
(52) U.S. Cl. .......................... 562/828; 562/833; 549/43; 549/57; 549/64; 558/13; 435/5; 435/6; 435/91.1; 435/91.2; 536/22.1; 536/23.1
(58) Field of Search ............................... 435/5, 6, 91.1, 435/91.2; 536/22.1, 23.1; 562/828, 833; 549/43, 57, 64; 558/13

(56) References Cited

U.S. PATENT DOCUMENTS 5,859,297 A * 1/1999 Matsumoto et al. ........ 562/828

* cited by examiner

*Primary Examiner*—Jezia Riley
(74) *Attorney, Agent, or Firm*—Leydig, Voit & Mayer, Ltd.

(57) ABSTRACT

A method for analyzing an objective substance, comprsing reacting a labeled probe with an objective substance on a biological sample, said probe comprsing a label substance of the formula (I):

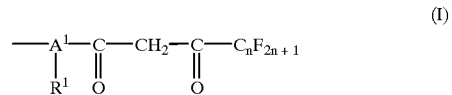

wherein $A^1$ is an aromatic group, $R^1$ is a hydrogen or $-COCH_2COC_nF_{2n+1}$ and n is an integer of 1–6, which is bonded to a probe selected from the group consisting of nucleic acid, nudeic acid binding potein, low molecular ligand and receptor for ligand (except antibody) to give a fluorescent complex, reacting the complex with an objective substance on a biolgical sample and assaying fluorescence of the resultant fluorescent complex, a labeled nucleic acid probe and a labeled nucleotide. According to the method of the present invention, defects such as hindrance of fluorescence due to contaminant substance, low sensitivity and the like can be resolved, thereby enabling analysis on a tissue.

23 Claims, No Drawings

ASSAY OF SUBSTANCE IN BIOLOGICAL SAMPLE USING LABELED PROBE

FIELD OF THE INVENTION

The present invention reates to a novel in situ assay method for an objective substance in a biological sample, comprising assaying on said biological sample, a reagent therefor, particularly a novel labeled nucleic acid probe and a fluorescent complex comprsing said probe and a heavy metal ion, a labeled nucleotide for preparing said labeled nudeic acid probe and a process for preparing said labeled nucleic acid probe. More particularly the present invention relates to a novel method which can be preferably used for analyzing the function and behavior of a certain substance (e.g., nucleic acid) on a biological sample (e.g., a biological tissue and a cell), by assaying the localization or concentration thereof on the biological sample, as well as a labeled probe and a reagent for analysis which contains said probe to be used for said method.

BACKGROUND OF THE INVENTION

In the research field of life science and the field of clinical diagnostic and clinical tests, fluoresct substances have been widel used as a label substance, besides radioactive substances, enzmes and the like. With the progress of the image analyzing technique systems in recent years they have been more increasingly used in a broad range of applications, thereby providing new findings in the function and behavior of biological substances in a living body.

Such fluorescent substances typically indude compounds comprising fluorescein, dansyl group, anthraniloyl group, pyrene, rhodamine, nitrobenzoxadiazol and the like.

The fluorescent substances, which are intercalated in between double strands of nucleic acid (DNA) and enable fluorescent staining of the DNA, include Hoechst 33342 manufactured by Molecular Probe, 4',6'-diamino-2-phenylindol dihydrochioride (DAPI), propidium iodite (PI), acridium orange and the like. Besides these, commercially available products such as SYTO (TM), BOBO (TM), POPO (TM), TOTO (TM), YOYO (TM) and the like are used similarly.

To label lipids, fluorescent substances, such as 4-nitrobenzene-2-oxa-1,3-diazol (NBD) and 4,4-difluoro-4-bora-3a,4a-diaza-s-indacene (BODIPY), are used.

In recent years, fluorescent substances capable of labeling various ions or other low molecular substances (e.g., fura-2, indo-1, fluo-3, etc. for calcium ion, SBFI, etc. for sodium ion, mag-fura-2, mag-indo-1, etc. for magnesium ion, TSQ, etc. for zinc ion, SPQ, etc. for chloride ion and FICRhR for cyclic AMP) have been developed, and the behavior of ions in a living body has been studied using these fluorescent substances.

In an assay of a substance in a biological sample, it is desired of a fluorescent substance, theoretically and practically, that (1) it does not deactivate nucleic acid, peptide, low molecular ligand and the like after binding, (2) it has a high fluorescence quantum yield and high photostability, (3) its fluorescence lifetime is long, (4) it is free of the effect of other endogenous fluorescent substances in the biological sample, (5) it does not react non-specifically with an endogenous molecule in the biological sample, (6) it easily dissolves in water and (7) its determination is convenient. Particularly, in an in situ assay on a tissue or cell, a fluorescent substance is further required to not react non-specifically with a biomolecule present in the tissue or cell or on the surface thereof.

However, some of the above-mentioned fluorescent substances are unstable to light and/or heat, some have low quantum yield, and others have short excited fluorescent lifetime and are subject to the effect of autofluorescence of other endogenous substances. The conventionall known fluorescent substances are not ideal fluorescent compounds, but rather, are insufficient, since they are more or less problematic in one or more aspects, such as low S/N ratio, short fluorescence wavelength and the like.

The influence of endogenous fluorescence in the assay of substances in a liquid sample such as body fluid and cell extract can be removed by using, as a lanthanoide metal-containing fluorescent complex, a complex labeled with a novel fluorescent substance and consisting of a substance having affinity for the objective substance and an europium ion. A method has been developed which is free of an influence of the background fluorescence derived from a fluorescent substance or non-fluorescent substance in a biological sample, particularly a serum, during assay of a physiologically active substance in the sample, and which comprises subjecting the complex to a time-resolved fluorescence assay.

For example, use of a diazaophenyl-EDTA-europium complex or isothiocyanatephenyl-EDTA-europium complex for an immnoassay has been known (*Anal. Biochem.* 137, 335–343, 1984). In this immnoassay, β-naphthoyltrifluoroacetone (β-NTA) is added to the assay system in the co-existence of β-diketone and tri-n-octylphosphine oxide (TOPO) to achieve the highest sensitivity.

This assay system has been known as a DELFIA system (Dissociation Enhanced Lanthanide Fluoroimmunoassay). A method utilizing a europium complex represented by this system is advantageous in that an assay target in a biological sample can be detected without the influence of fluorescence having a short lifetime which is derived from a contaminating substance in the body, due to the fluorescent property of this complex that its life is long.

On the other hand, the DELFIA system is associated with the defect caused by a reaction between β-NTA or TOPO used for the assay and europium in a sample or in the environment, thereby producing strong fluorescence, which may prevent detection of the assay target In addition to the inherent defect this system has in that it is susceptible to the influence of the contaminated europium, the need to add a fluorescence intensifier such as β-NTA makes the assay on a solid phase unattainable. There is also a problem of manipulative complexity due to the step of adding a fluorescence intensifier. In conclusion, in situ asssy of a physiologicaly active substance (e.g, nucleic acid, receptor, sugar chain, ganglioside and the like) fixed on a tissue or cell (surface) by this system is extremely difficult.

To resolve the above-mentioned defects of the DELFIA system, a Cyber Fluor system that uses a complex of 4,7-bis-(chlorosulfophenyl)-1,10-phenanthroline-2,9-dicarboxylic acid (BCPDA) and europium is known (*Anal. Chem.*, 61, 48–53, 1989).

The use of BCPDA has made a great advancement in that nany europium fluorescent complexes can be introduced without a quenching phenomenon (quenching phenomenon strikingly deceases the fluorescence quantum yield) caused when one probe is labeled with many fluoresceins and that it is highly stable and can resolve the defects of the DELFIA system.

However, the Cyber Fluor system has a fatal defect in that its sensitivity is lower than that of the DELFIA system by the order of two digits or more. To compensate for the defect, synthesis of a number of europium complexes was tried, and, for example, trisbipyridine cryptate (TBP) europium complex and the like are known (*Clin. Chem*, 196–201, 1993, U.S. Pat. No. 5,262,526, JP 07-10819 A and the like). These newly developed europium fluorescent complexes have defects in that they have short excitation wavelengths and weak fluorescence, and they require many synthetic steps. Thus, they do not have particulary superior property as compared to the above-mentioned two europium fluorescent complexes.

Many studies have been made so far with respect to europium fluorescent complex and it has been found that β-diketone-europium fluorescent complex has greater fluorescence intensity than aromatic amine-europium complex, and of the β-diketone ligands, a europium fluorescent complex of 2-naphthoyltrifluoroacetone (β-NTA) and 2-thenoytrifluoroacetone (TTA) particurlaly has the greatest fluorescence intensity.

The present inventors snthesized various β-diketone-europium TOPO complexes to study the effect of β-diketone as a substituent on the fluorescence property of the β-diketone-europum fluorescent complex, and found that the fluorescence intensity of these complexes is dependent on the composition and structure of the substituents $R^1$ and $R^2$ of the β-diketonato ($R^1COCH_2COR^2$). In other words, when $R^1$ is an aromatic hydrocarbon residue, stronger electron attractiveness of $R^2$ results in stronger fluorescnce intensity of the complex, based on which finding an immunoassay utilizing a β-diketone type europium fluorescent complex having a dramatically improved fluorescence intensity has been found (U.S. Pat No. 5,859,297 and *Anal. Chemi.*, 70, 596–601, 1988).

However, the use of this β-diketone type europium fluorescent complex for the assay of a substance having various actions that is on a bioloical tissue or cell, such as a physiologically active substance, has not been disclosed. Many difficulties are foreseeable in an assay on a tissue or cell of a physiologically active substance in the biological sample, for exnple, a great influence of contaminating substance, a difficult high sensitivity assay, an unattainable easy assay and the like.

It is therefore an object of the present invention to provide a means of resolving defects such as hindrance of fluorescence by a contaminating substance and low sensitivity, so that a substance in a tissue or cell or on surface thereof, such as nucleic add, nucleic acid binding protein, receptor, sugar chain, ganglioside and the like can be assayed as it is on the tissue or cell with high precision and high sensitivity.

SUMMARY OF THE INVENTION

The present invention is based on the finding that β-diketone form europium fluorescent complex has superior characteristics as a label for probe for the high sensitivity assay of a physiologicly active substance such as nucleic acid, nucleic acid binding protein, receptor, enzyme, sugar chain, ganglioside and the like on a tissue or cell, since it has a noticeably long fluorescence lifetime and permits time-resolved fluorescence assay, assay upon elimination of blank fluorescence, use in one step and has a long wavelength fluorescence lifetime.

Accordingly, the present invention provides a method for analyzing a biological substance comprising the use of a label substance of the following formula (I):

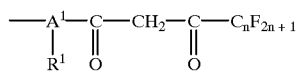

wherein $A^1$ is an aromatic group, $R^1$ is a hydrogen or $-COCH_2COC_nF_{2n+1}$ and n is an integer of 1–6, or a label substance of the following formula (II)

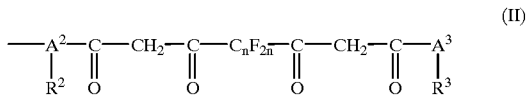

wherein $A^2$ and $A^3$ are the same or diferent and each is an aromatic group, $R^2$ and $R^3$ are the same or different and each is a hydrogen or $COCH_2COC_nF_{2n+1}$ and n is an integer of 1–6, reagents therefor and a preparation method thereof. More partcularly, the present invention provides the following.

(1) A method for analyzing an objective substance, comprising reacting a labeled probe with an objective substance on a biological sample, said probe comprising a label substance of the formula (I) or a lab substance of the formula (II) bonded to a probe selected from the group consisting of nucleic acid, nucleic acid binding protein, low molecular ligand and receptor for ligand (except antibody) via a cross-linking group or a cross-linking group and a conjugating group, adding a heavy metal ion and assaying fluorescence of the resultant fluorescent complex.

(2) The method for analyzing an objective substance, comprising adding a heavy metal ion to a labeled probe, said probe comprising a label substance of the formula (I) or a label substance of the formula (II) bonded to a probe selected from the group consisting of nucleic acid, nucleic acid binding protein, low molecular ligand and receptor for ligand (except antibody) via a cross-linking group or a cross-linking group and a conjugating group to give a fluorescent complex, reacting the complex with an objective substance on a biological sample and assaying fluorescence of the resultant fluorescent complex (3) A labeled nucleic acid probe comprising a label substance of the formula (I) or a label substance of the formula (II) bonded to a nucleic acid probe via a cross-linking group.

(4) A fluorescent complex comprising the labeled nucdeic acid probe of (3) and a heavy metal ion.

(5) A reagent for analyzing a nucleic acid, comprising the labeled nucleic acid probe of (3).

(6) A labeled nucleotide comprising a label substance of the formula (I) bonded to a nucleotide via a cross-linking group.

(7) A fluorescent complex comprising the labeled nucleotide of (6) and a heavy metal ion.

(8) A method for producing a labeled nucleic acid probe comprising reacting the labeled nucleotide of (6), dNTPs and a single strand DNA in the presence of a DNA polymerase.

(9) A method for producing a labeled nucleic acid probe comprising reacting the labeled nucleotide of (6), dNTPs and a double stranded DNA in the presence of 5'-exonuclease, DNase and a DNA polymere.

(10) A labeled nucleic acid probe obtained by the production method of (8) or (9).

(11) A reagent for analyzing nucleic acid comprising a label substance of the formula (I) or the formula (II), to which avidin is covalently bonded via a cross-linking group (hereinafter to be refereed to as label substance A) and a nucleotide to which biotin is bonded via a linkage group (hereinafter to be referred to as nucleotide B).

(12) A method for analyzing an objective substance comprising reacting the objective substance with a nucleic acid probe comprising the nucleotide B as a component on a biological sample and then with the label substance A, adding a heavy metal ion and assaying the fluorescence of the resultant fluorescent complex According to the method of the present invention, defects such as hindrance of fluoresence by a contaminating substance and low sensitivity can be resolved in the analysis of nucleic acid, nucleic acid binding protein, receptor, sugar chain, ganglioside and the like on a biological tissue, cell or chromosome in a biological sample. In particular, hindrance due to contamination with a lanthanoide metal ion in a sample or environment can be removed, and assay of the objective substance with high sensitivity and with small steps.

DETAILED DESCRIPTION OF THE INVENTION

The label substance in the present invention is represented by the formula (I) or the formula (II). In the formulas, $A^1$, $A^2$ and $A^3$ are the same or different and each is a trvalent aromatic group, particularly a conjugated double bond, wherein when $R^1$, $R^2$ or $R^3$ is hydrogen, $A^1$, $A^2$ or $A^3$ it binds with is a divalent aromatic group. Such divalent or trivalent aromatic group is exemplified by

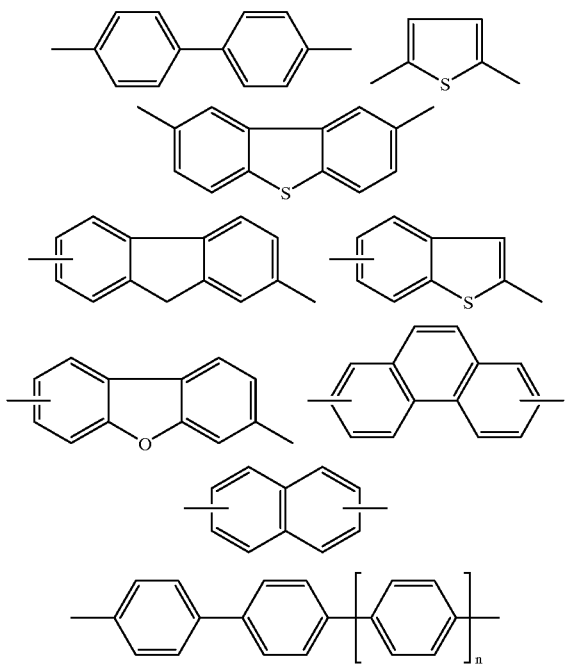

and the like. Those having a substituent to these aromatic rings, such as methylphenylene and methyldibenzothiopehne, are also exemplified.

Particularly preferable aramatic group is the following

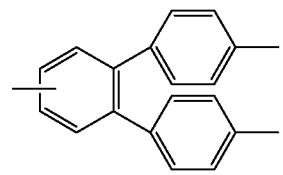

$R^1$, $R^2$ and $R^3$ are each independently hydrogen or $COCH_2COC_nF_{2n+1}$.

In the formulas (I), (II) and (III), n and n at $R^1$, $R^2$ and $R^3$ are an integer of 1–6, preferably 2–4.

In the present invention, a particularly preferable label substance is represented by the formula (III):

(III)

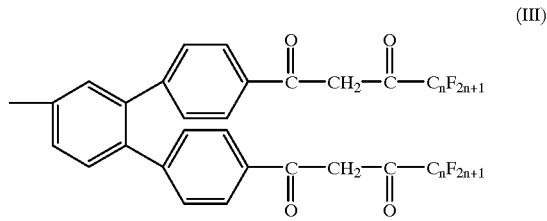

wherein n is an integer of 1–6.

In the present invention, the probe is selected from the group consisting of nucleic acid, nucleic acid binding protein, ligand and receptor for ligand (except antibody).

In the present invention, the obective substance is a component in the biological sample, which is to be the subject of the analysis. Preferable examples thereof include nucleic acid, nucleic acid binding protein, ligand, receptor for ligand and the like.

The nucleic acid binding protein is a protein that specifically binds with the nucleic add having a specific nucleotide sequence, such as histone, DNA binding protein, Lac I protein and the like. By the use of a transcription regulating factor of cytokine (a kind of DNA binding proteins), such as NF-κB and the like, as a probe to be labeled, the interaction between the transcription factor and DNA can be visualized.

The low molecular ligand here means an organic compound such as sugar chain, aromatic compound, ganglioside, oligosaccharide, peptide consisting of 2–10-amino acids and the like. Examples thereof include myc peptide, thyroxine, triiodothyroine, ganglioside GM2, cellobiose, sugar chain having a sialic acid at the end thereof and the like.

The receptor for ligand means a substance that specifically binds with a specific ligand that is located on or in a cell or between cells, such as cellulose binding protein, sialic acid binding lectin, albumin receptor and the like.

Further examples of the low molecular ligand or receptor include hormone or hormone receptor such as insulin, insulin receptor, EGF, EGF receptor, HGF, HGF receptor, TSH, TSH receptor and the like, and receptors of low molecular ligands such as receptor of cytokine (e.g., IL-8 and the like) or chemokine, acetylcholine receptor, histamine receptor and the like.

The protein kInase C can bind with the derivative of phorbol ester and can be assayed by the method of the present invention. In addition, the enzymes such as cAMP-dependent protein kinase, cGMP-dependent protein kinase, calmodulin-dependent phosphoenzyeme, tyrosine-phosphorylated enzyme and the like can be assayed by way of and-receptor reaction, wherein the labeled probe of the present invention can be used as the probe for the substrate binding site of the engyme.

Various lectins against various sugar chain and ganglioside can be used as the probe of the present invention. Examples of lectin include concanavalin A against D-mnannose bonded with various proteins on the cell, wheat germ agglutinin against di-N-acetylchitobiose, sialic acid binding lectin against sialic acid, which is derived from Limulus polyphemus and the like.

Examples of nucleic acid and nucleic acid probe include DNAs having a series of various deoxyribonucleic acids (dATP, dGTP, dTTP, dCTP, dUTP) and RNAs having a seies of various ribonucleic acids (rATP, rGTP, rTTP, rCTP, rUTP). These nucleic acid probe has a nucleotide sequence consists of cDNA or antisense oligonucleotides that specifically hybridizes with mRNA which expresses in the cell. Alternatively, a nucleic acid probe having a nucleotide sequence complementary to a part of a specfic sequence of nucleic acid or chromosome in the cell can be used.

Examples of the nucleic acid or gene on chromosome in the cell include oncogene (e.g, abl erb, fos myb, myc, ras, src and the like), tumor suppressor gene (e.g., p53 and the like), rearranged T cell receptor gene, rearranged immunoglobulin gene, a part of the nucleotide sequence of pathogenic virus gene such as Epstein-Bar virus (EBV), herpes simplex virus (HSV), cytomegalovirus (CMV), hepatitis B virus (HBV), rotavirus, adenovirus and the like, a part of the nucleotide sequence of infectious pathogenic microrganism gene such malaria protozoa, fungus, mycoplasma and the like, and nucleic acid having a nucleotide sequence complementary thereto.

A part or the whole of the nucleic acid probe complementary to these genes or homologous therewith may have a modified group such as methyl group and the lie as long as it does not affect bonding with a label substance.

The labeled nucleic acid probe of the present invention is a compound having affinity for a specific substance particularly on the tissue or cell, such as nucleic acid, nucleic acid binding protein and the like containing the above-mentioned genes on chromosome and the like.

The labeled probe in the present invention consists of a probe selected from the group consisting of nucleic acid, nucleic acid binding protein, low molecular ligand and receptor for ligand (except antiboydy) and a label substance bonded thereto. The labeled nucleic acid probe of the present invention consists of a nucleic acid and a label substance bonded to each other. The labeled nucleotide of the present invention consists of a nucleotide and a label substance bonded thereto. The bond between the label substance and the probe or nudeotde is a bond via a cross-linking group. It may be a covalent bond via a conjugating group.

The cross-linking group is via a bond between a label substance and a conjugating group, probe, nucleotide or avidin. That is, in a labeled probe and a labeled nudeotide having a conjugating group, the conjugating group exists between the cross-linking group and the probe or nudeotide.

The label substance A in the present invention consists of avidin and a label substance bonded via a cross-linking group. The binding ratio of avidin-label substance is 1–50, preferably 2–30. The nudeotide B in the present invention consists of biotin and nucleotide bonded via a linkage group.

Avidin in the present invention is a glycoprotein that is contained in the egg white and specifically binds with biotin. Avidin may be a streptoavidin derived from a microorganism (genus Streptococcus) or a reombinant protein thereof.

Biotin in the present invention is a substance called vitamin H and coenzyne R and binds extremely with avidin or steptoavidin, wherein the bonding strength is far greater than the bond of typical immunoconjugate.

The cross-linking group in the present invention is derived from a group capable of bonding with both nucleic acid, nucleic acid binding protein, low molecular ligand, receptor for ligand, nucleotide or avidin and aromatic group. Alternatively, it is derived from a group capable of bonding with both linkage group and aromatic group.

Examples of the cross-linking group include —NH—CS—, —NH—CO—, —CO—, —N$_2$—, —NH—, —SO$_2$—, —CH$_2$—S—, —CH$_2$—NH—, —(CH$_2$)$_6$—NH—CO—CH$_2$—CH$_2$—CO—, and S—S— and the like. Faticularly preferable cross-linking groups are sulfonyl group and carbonyl group.

The linkage group in the present invention is free of particular limitation as long as it connects a cross-linking group and a nucleic acid, nucleic acid binding protein, low molecular ligand, receptor for ligand or nucleotide. Preferable linkage group is a divalent aliphatic hydrocarbon group having 5–25 carbon atoms and 7 or less amide bonds between carbons Specific examples include a group of the formula (IV):

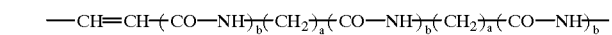

(IV)

wherein a is an integer of 0–6 and b is 0or 1.

Another preferable mode of the linkage group is a linkage group containing biotin and avidin through affinity binding.

Biotin affinty binding with avidin is preferably further bonded to a probe via a linkage group. Examples of preferable linkage group include divalent aliphatic hydrocarbon group having 5 to 25 carbon atoms and optionaly having 7 or less amide bonds between carbons. Specifically, it is —H═CH—CO—NH—CH$_2$—CH$_2$—NH—(CO—CH$_2$—CH$_2$—CH$_2$—CH$_2$—NH)$_2$—, wherein preferable bond is (probe) -CH═CH—CO—NH—CH$_2$—CH$_2$—NH—(CO—CH$_2$—CH$_2$—CH$_2$—CH$_2$—CH$_2$—NH)$_2$—, biotin:avidin-(cross-linking group-label substance).

The linkage group binding biotin and nucleotide in nucleotide B is free of limitation as long as it binds biotin and nucleotide. Prferable linkage group include a divalent aliphatic hydrocarbon group having 5 to 25 carbon atoms and optionaly having 7 or less amide bonds between carbons. Specifically, it is —CH=CH—CO—NH—CH$_2$—CH$_2$—NH—(CO—CH$_2$—CH$_2$—CH$_2$—CH$_2$—CH$_2$—NH)$_2$—, wherein preferable bond is (nucleotide) -CH=CH—CO—NH—CH$_2$—CH$_2$—NH—(CO—CH$_2$—CH$_2$—CH$_2$—CH$_2$—CH$_2$—NH)$_2$-(biotin.

When the label substance of the formula (II) is bonded to probe or avidin via two cross-linking groups, the two cross-linking groups may be the same or different. Again, when it is bonded to probe or avidin via two conjugating groups, the two conjugating group may be the same or diferent.

The label substance of the formula (II) can be used upon binding to two probes or avidin. The two probes may be the same or different two probes or avidin. By binding to two probes, a synergistic binding effect can be expected.

For example, one example of the labeled nucleic acid probe of the present invention is a label substance bonded to different nucleic acid probes. These probes are nucleic acid probes having nucleotide sequences complementary to or homologous with the same or different genes in other words, a probe having plural nucleic acids recognizing the specific sites of the assay target binds with the nucleic acid in the cell having nucleotide sequences complementary hereto or nucleotide sequences homologous therto and becomes a so-called divalent probe by forming a fluorescent complex upon addition of a heavy metal ion (e.g., lanthanoide metal ion), thereby affording a possible synergistic effect.

Even when the two binding probes are the same, each can bind with an objective substance haing same plural specific sites. Thus, the effect is not a simple addition but expected to be synergistic.

In the analysis method of the present invention, different kinds of labeled probes may be used simultaneously upon mixing.

While the binding ratio of the probe-label substance is free of particular limitation, it is generally 1–100, preferably 1–20.

The binding ratio of the nucleotide-label substance is free of particular limitation, it is generally 1–50, preferably 1–20.

The binding ratio of the avidin-label substance is free of particular limitation, it is generaly 1–50, preferably 2–30.

The labeled probe, labeled nucleotide or label substance A can be produced by the use of the following functional groups as long as it does not exert an adverse influence, for binding a label substance to the probe, nucleotide or avidin. For example, various binding groups such as isothiocyanate group reactive with amino group, sulfonyl halide group (sulfonyl chloride group, sulfonyl fluoride group and the like), o-phthalaldehyde group in the presence of 2-mercaptoethanol, N-substituted maleimide group and the like for carbodiimide group and thiol group, iodoacetamide group for histidine and the like.

Specificafly, a ligand, nucleic acid and the like and a labeling compound of the following formula in a molar amount of 1–20 per mol of ligand, nucleic acid and the like a reacted in a solvent.

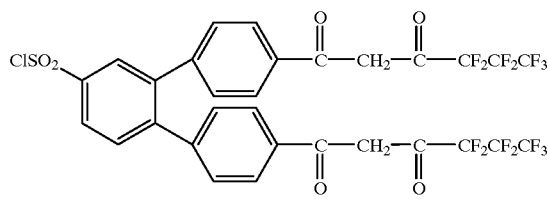

The present invention also relates to a fluorescent complex containing a labeled nucleic acid probe and a heavy metal ion. Examples of the heavy metal ion include lanthanoide metal ion and radium ion, with preference given to lanthanoide metal ion. The lanthanoide metal ion to be used in the present invention incdudes ions of europium (Eu), samarium (Sm), terbium (Tb), dysprosium (Dy) and the like. It is typically used in the form of a chloride, but may be used in the form of other salts as long as the assay is not influenced. in the present invention, these lanthanoide metal ions may be used alone or in combination.

The reaction between the labeled probe and the objective substance in the present invention is the reactions between nucleic acid and nucleic acid, nucleic acid and nucleic acid binding protein, and ligand and receptor for ligand in a biological sample. For facilitated reaction, the biological sample may be pre-treated. For example, nucleic acid extraction by AGPC, protein dissociation treatment with ethanol and the like can be applied.

The biological sample is preferably a cell, tissue or chromosome.

The analysis method of the present invention analyzes the objective substance in the cell and on the cell surface, wherein a labeled probe is reacted with the objective substance at a tissue section, on a cell surface, on a chromosome and the like, a heavy metal ion such as lanthanoide metal ion, radium ion and the like is added and fluorescence of the resultant complex is assayed, or a heavy metal ion such as lanthanoide metal ion, radium ion and the like is added to a labeled probe to give a fluoresent complex, which is reacted with the objective substance on a biological sample and fluorescence of the complex after reaction is assayed.

The analysis method of the present invention may comprise reacting a nucleic acdd probe containing nucleotide B as a component with the objective substance on a biological sample, then reacting with label substance A, adding a heavy metal ion, and assaying fluorescent of the resultant fluorescent complex The nucleic acid probe containing nucleotide B as a component means that one or more nucleotides in the nucleotide sequence is(are) nucleotide B. Namely, it is a nucleic acid probe binding with biotin.

The nucleic acid probe containing nucleotide B as a component can be obtained by reacting nucleotide B, dNTPs and single strand DNA in the presence of a primer and a DNA polymerase to give a double stranded DNA and denaturing the obtained DNA with heat to give a single strand DNA.

The nucleic acid probe containing nucleotide B as a component can be obtained by reacting nucleotide B, dNTPs and a double stranded DNA in the presence of 5'-exonuclease, DNase and a DNA polymemse to give a double stranded DNA and denaturing the obtained DNA with heat to give a single strand DNA.

More specific analysis method is exemplfied by the method comprising immersing a biological sample in a buffer containing a labeled probe, incubating the sample to allow reaction of the objective substance and the labeled probe, washing off excess beled probe with the buffer, immersing the probe in a buffer containing lanthanoide metal ion to form a complex and assaying the fluorescence of the resultant complex In addition, a method is exemplified, which comprises admixing buffer containing lanthanoide metal ion with a buffer containing a labeled probe to form a complex, immersing a biological sample in this mixture, incubating the sample to allow reaction with the objective substance, washing off excess (labeled probe: lanthanoide metal ion) complex and assaying the fluorescence of the resultant complex on the biological sample.

As a different specific method, the following method is exemplified. That is, a double stranded DNA having a sequence to be the assay target, nucleotide B and dNTPs are reacted in the presence of 5'exonuclease, DNase and a DNA polymerase to give a biotin-bound nucleic acid probe. A biological sample is immersed in a buffer containing this biotin-bound nucleic acid probe and incubated to allow reaction of the objective substance and the biotin-bound nucleic acid probe, and excess biotin-bound nucleic acid probe is washed off. Then, the sample is immersed in a buffer containing the label substance A to bind biotin and avidin, and excess label substance A is removed. Then, the sample is immersed in a buffer containing lanthanoide metal ion to form a complex and the fluorescence of the resultant complex is assayed.

By these methods, the presence of the objective substance in a biological sample such as a tissue, cell, chromosome and the like is visualized and analyzed for localization and concentration. In addition, abnormalities with respect to the objective substance can be analyzed.

The visualized image obtained by the use of the inventive labeled probe can be retained through a fluorescence microscope, confocal laser-scanning microscope and the like. The fluorescence signal itself is assayable with a fluorescence assay device, time-resolved fluorescence assay device and the like.

In particular, the inventive labeled nucleic acid probe is reacted with a biological sample of a tissue, cell, chromosome and the like and visualize the objective substance therein by colony hybridization, fluorescence in situ hybridization (FISH) of tissue and chromosome, nucleic acid sandwich hybridization, comparative genome hybridization (CGH) and the like.

The present invention also relates to a labeled nucleotide. The nucleotide of the present invention itself has affinitity with a specific substance on a tissue or cell. It may be used to produce a labeled nucleic acid probe by binding with a different nucleotide or by nick translation method from a double stranded DNA.

The nucleotide in the labeled nucleotide and nucleotide of nucleotide B of the present invention is not particulriy limited and is exemplified by ATP, GTP, CTP, UTP, dATP, dGTP, dCTP, dTTP, dUTP and the like, with particular preference given to dUTP.

The particularly preferable labeled nucleotide has the following formula (V):

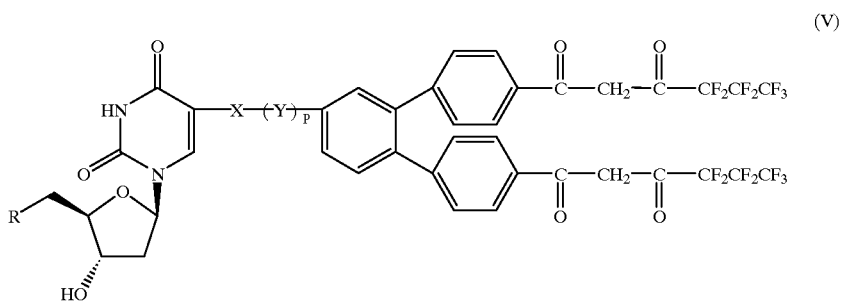

(V)

wherein X is a conjugating group of the formula (IV) and Y is a sulfonyl group or carbonyl group, R is a group of the formula

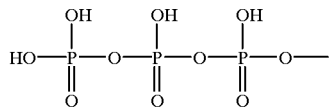

and p is 0 or 1.

The present invention further relates to a fluorescent complex containing the above-mentioned labeled nucleotide and a heavy metal ion. Examples of the heavy metal ion include the above-mentioned lanthanoide metal ion and radium ion, with preference given to the above-mentioned lanthanoide metal ion.

A labeled probe can be obtained by incorporating a labeled nucleotide such as the labeled dUTP of the present invention and the like, when synthesizing a fargmented probe DNA using DNA exracted from the tissue or cell, particularly chromosomal DNA. To be specific, labeled nucleotide, dNTPs and double stranded DNA is reacted in the presence of 5'-exonuclease, DNase and a DNA polymerase to give a labeled nucleic acid probe. Alteratively, a labeled nucleotide, dNTPs and a single strand DNA are reacted in the presence of a DNA polymerase to give a laeled nucleic acid probe. Particularly preferably, labeled nucleotide of the present invention, such as labeled dUTP and the like is incorporated by nick translation method to give a DNA or a DNA fragnent usable as a labeled nucleic acid probe.

Moreover, labeled nucleic acid probe, labeled nucleotide or nucleotide B of the present invention can be incorporated into DNA or RNA by nucleic acid amplification by PCR (polymerase chain reaction) method, LCR (ligase chain reaction) method, NASBA method and the like. The obtained DNA or RNA can be used for the analysis of the objective substance as a labeled nucleic acid probe or a biotin-bound nucleic acid probe.

The nucleic acid probe obtained by incorporating the labeled nucleotide or nucleotide B of the present invention, that comprises a DNA complementary to the DNA of a tissue or cell can be particulary suitably used for the analysis of abnormalites in the chromosome of the objective tissue or cell.

The reagent for the analysis of nucleic acid of the present invention contains the above-mentioned novel labeled nucleic acid probe or labeled nucleotide. Preferably it contains a heavy metal ion such as the above-mentioned lanthanoide metal ion, radium ion and the like.

The reagent for the analysis of nucleic acid of the present invention contains label substance A and nucleotide B. The reagent containing label substance A and nucleotde B preferably further contains dNTPs, primer, DNA polymerase and heavy metal. As a different mode, a reagent containing label substance A and nucleotide B preferaly further contains dNTPs, 5'-exonuclease, DNase, DNA polymemwe and heavy metal.

The present invention is explained in detail by illustrative reference examples and examples, to which the present invention is not limited in any way.

Reference example 1
Synthesis of 4,4'-diacetyl-o-terphenyl

To a solution of $CH_2Cl_2$ (200 ml), $AlCl_3$ (210 mmol) and $CH_3COCl$ (205 mmol) was gradually added a solution of $CH_2Cl_2$ (100 ml) and o-terphenyl (100 mmol) dropwise with sag at 0° C. The mixture was stired at 0° C. for 30 min and further stired at room temperature for 24 hr. The reaction solution was refluxed for 2 hr, and then poured into cornc. hydrochloric acid with ice. The mixture was sufficiently stirred, and $CH_2Cl_2$ was distilled away under reduced pressure. The precipitate was separated by filtration, and thoroughly washed with water. The product was recrystallized from 2-butanone (about 250 ml) to give needle crystals, which were separated by filtration and dried in. vacuo. The yield was 22.1 g (70.3%). The results of elemental analysis were as follows.

Element analysis: calculated: C%=84.05, H%=5.77; found: C%=84.96, H%=5.87.

Reference example 2
Synthesis of intermediate of labeled compound

The intermediate having the following structure was synthesized.

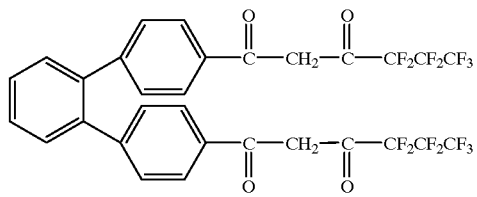

To anhydrous ether ($Et_2$, 30 g) were added $NaOCH_3$ (3.0 g), 4,4'-diacetyl-o-terphenyl (10 mmol) and $C_3F_7COOC_2H_5$ (20 mmol), the mixture was stirred in a sealed container at room temperature for 24 hr. Anhydrous ether was distilled away to give a residue, which was dried in vacuo for 30 min. The product was neutralized with 15% sulfuric acid (100 ml), and the precipitate was separated by filtration and washed well with water. The precipitate was dissolved in ethanol (200 ml) under heating and the insoluble substance was removed by filtration. The solution was concentrated to about 20 ml under reduced pressure. This solution was gradually added dropwise to petroleum ether (200 ml) under stirring. The mixture was suffciently stirred and filtered to remove a small amount of deposited precipitate. The filtrate was evaporated to completely remove the organic solvents. The obtained oily substance was dried in vacuo to give a yellow powder. The product was dried in vacuo for 24 hr. The yield was 460 g (65.0%).

Elemental analysis: calculated: C%=51.00, H%=2.28; found: C%=51.22, H%=2.61; $^1$H—NMR confirmed that the product was the objective compound.

Reference example 3
Synthesis of labeled compound

The labeled compound having the following structure was synthesized.

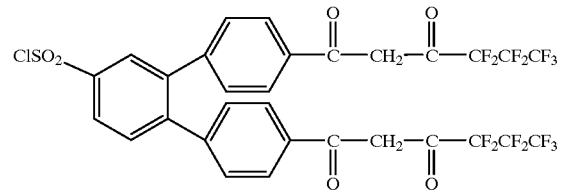

To chlorsulfuric acid (3.5 ml) was grdually added β-diketone (the intermediate obtained in Reference example 2, 2 mmol) under stirring at room temperature. The reaction mixture was stirred at room temperature for 7 hr, then carefully added dropwise to ice water (150 ml, outside cooled with ice water) under stirring. The resultant precipitate was immediately centrifuged, washed with cold water (about 5° C. and centrifuged twice. The precipitate was suspended in a small amount of cold water and transferred onto a glass filter, and water was removed by suction filtration. The resultant chlorosulfonylated β-diketone was dned in vacuo at room temperature for 48 hr or more. The yield was 77%.

Elemental analysis: calculated: C%=44.76, H%=1.88; found: C%=44.50, H%=1.92; $^1$H-NMR confirmed that the product was the objective compound.

EXAMPLE 1
Labeling of p53 , Human, Probe (exon 4 translated) a labeled compound

The labeled compound obtained in Reference Example 3 and p53, Human, Probe (exon 4 translated) manufactured by Oncogene Research Product (Cosmo Bio) were reacted in the following manner to prepare a labeled DNA wherein said labeled compound is bound with p53, Human, Probe mediated by a sulfonyl group.

One hundred pmol of p53, Human, Probe (exon 4 translated) was dissolved in 0.1 mol/l carbonate buffer solution (pH=9.3, 100 µl). To this DNA solution was gradually added a solution (10 µl ) of the labeled compound having a mole number equal to said nucleic acid (having about 280 amino groups/molecule) dropwise under stirring at room temperature. The mixture was stirred at room temperature for 1 hr, extracted with phenol/chloroform, and subjected to ethanol precipitation. The precipitate was washed with 80% ethanol and dried. The dried precipitate was re-dissolved in 0.05 mol/l carbonate buffer solution (pH=8.0, 100 µl).

The molarly of the labeled compound contained in this solution was calculated. In addition, the molar absorption coefficient of the labeled compound at 330 nm was calculated from the absorbance at 330 nm. As a result, the absorption coefficient was 0.97 mol$^{-1}$cm$^{-1+1}$. There was no absorption by DNA at 330 nm. Assuming that molar absorption coefficient does not change during the process of labeling reaction, the concentration of the label in the labeled DNA solution and the binding ratio of the label and DNA were calculated.

The binding ratio of DNA to the labeled compound obtained by the above method was about 1.

EXAMPLE 2

Hybridization of the labeled DNA with genes in a liver tissue

A liver tissue excised from human was fixed with 4% paraformaldehyde-PBS at 4° C. overnight, and dehydrated with 70%, 80%, 90% and 100% ethanol, successively. All water used in this experment was purified water treated with diethylpyrocarbonate (DEPC). Further dehydration was performed by exchanging the solution in the liver tissue twice with 100% ethanol. Then, the liver tissue was transferred into xylene, heated at 60° C. for 2 hr (3 times), and embedded with paraffin.

The section (about 5 μm) of this paraffin-embedded tissue was prepared using a microtome, placed on a thoroughly washed slide glass, and dried at 37° C. for 6 hr to give a section preperation. The section preparation was further dried with a drier, treated with xylene, 100% ethanol, 90% ethanol, 80% ethanol, 70% ethanol and phosphate buffer (PB, pH 7.4), successively, and treated with proteinase K solution (10 mM Tris-HCl (pH 8.0), 1 mM EDTA, 10 μg/ml) for 20 min.

The section preparation was then immersed in 4% paraformaldehyde-PB solution for 10 min, washed with PB, and treated with 0.2N hydrochloric acid for 10 min, with PB for 1 minute, with 0.1 M triethanolamine hydrocloric acid (pH 8.0) for 1 minute, with 0.1 M triethanolamine hydrochloric acid (pH 8.0) containing 0.25% acetic anhydride for 10 min, and with PB for 1 minute. The section preparation was further treated with 70% ethanol, 80% ethanol, 90% ethanol and 100% ethanol, successively, and air-died to give an air-dried sample. The air-dried sample was immediately subjected to the following hybridization.

As a hybridization solution, a solution comprising 50% formamaide, 10 mM Tris-HCl (pH 7.6), 10% dextran sulfate, 600 mM NaCl, 0.25% SDS, 1 mM EDTA, 200 μg/ml tRNA and 1×Denhard's solution was prepared.

The labeled DNA obtained in the Example was dissolved in this hybridization solution to the concentration of 5 ng/ml. The mixture (about 40 ml) was dropped onto the abave air-dried sample. Prior to hybridization, the sample was prehybridized with the hybridization buffer without the labeled DNA at 37° C. for 2 hr. Then, the air-dried sample was covered with parafilm (CAN Co.), and incubated at 37° C. for 16 hr in a moistuer chamber, in which a paper towel moistened with 50% formamide solution was set, for hybridization with the labeled DNA.

After hybridization, the parafilm was removed from the slide glass in 5×SSC solution (40° C.), and the slide glass having the section hybridized with the labeled DNA was heated in 2×SSC, 50% formamide at 40° C. for 30 min. The slide glass was washed with TNE solution (aqueous solution contaning Tris-HCl buffer, NaCl, and EDTA), and reacted with 5 μg/ml RNase A in TNE solution for 10 min.

The slide glass was then washed with 2×SSC at 40° C. for 20 min (once), and 0.2×SSC at 40° C. for 20 min (twice). Finally, the slide glass was immersed in 0.2×SSC solution (pH 8.5) containing 0.1 mM europium chloride to give a fluorescent complex from the reaction of the labeled DNA with europium chloride. The section on the side glass was observed with a fluorescence microscope.

As a result, signals derived from the fluorescent complex of the labeled DNA and europium chloride were detected on the section. When hybrdization was performed usng DNA labeled with fluorescein isothiocyanate (FITC) in the place of the labeled DNA above as a comparative example, hybridization signals were hardly detected. In this experiment, europium chloride was not added to detect the signals.

EXAMPLE 3

Preparation of a labeled PCR product

Two oligonucleotides (SEO ID: NO: 1 and SEQ ID: NO: 2), having the nucleotide sequences homologous to the sense and antisense sequence of hepatitis B virus surface antigen (HBsAg) gene, respectively, were synthesized by phosphoamidite method using an automatic DNA/RNA synthesizer. In the final step of the synthesis, a labeled compound was reacted with the 5' termini of the elongated oligonucleotides to give two kinds of labeled oligonucleotides shown in the following formulas (1) and (2).

Formula (1)

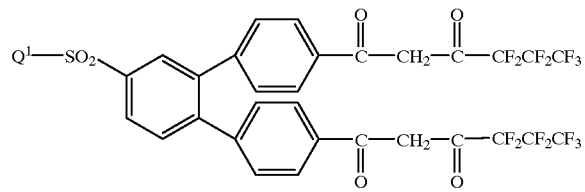

wherein $Q^1$ is oligonucleotide (SEQ ID: NO: 1) in which the amino group of the nucleotide at the 5' terminus binds to the sulfonyl group of the labeled compound.

Formula (2)

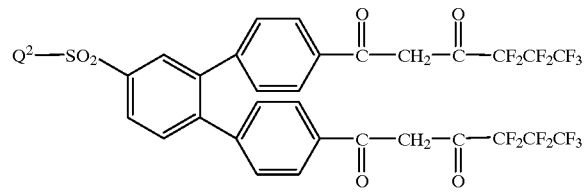

wherein $Q^2$ is oligonucleotide (SEQ ID: NO: 2) in which the amino group of the nucleotide at the 5' terminus binds to the sulfonyl group of the labeled compound.

Using the above two labeled oligonucleotides as a pair of primers and the nucleic acid fraction extracted with phenol/chloroform from the serum derived from a patient, who was strongly positive against HBsAg, as a template, PCR was carried out under the followng conditions.

A reaction mitur consisting of 10 mM Tris-HCl (pH 9.0), 50 mM KCl, 1.5 mM magnesium chloride, 0.1% Triton X-100, dNTPs (50 μM each), 0.02 U/μl Taq DNA polymerase, and primers (0.4 pM each) was used for amplification.

After preheating at 95° C. for 2 min, thermal denaturation was performed at 95° C. for 30 sec, annealing was performed at 57° C. for 30 sec, and elongation was performed at 72° C. for 80 sec. These steps were repeated 30 cycles to give a 600 bp DNA as a PCR product.

Addition of europium chloride to the DNA product resulted in the generation of extremely strong fluorescence.

EXAMPLE 4

Analysis of liver tissue using labled PCR product

A tissue section was prepared from the liver excised from a human infected with hepatitis B according to the method descmbed in Example 2, except the use of a normal sterlized purfied water in the place of DEPC-treated water, to give an air-dried sample on a slide glass.

A hybridization solution consisting of 50% formamide, 10 mM Tris-HCl (pH 7.6), 10% dextran sulfate, 600 mM NaCl, 0.25% SDS, 1 mM EDTA, 200 µg/ml tRNA and 1×Denhardt's solution, was prepared. Prior to hybridization, the air-dried sample was prehybridized with this hybridization solution without PCR amplification product for 2 hr.

The labeled PCR amplification product obtained in Example 3 was dissolved in this hybridization solution to the concentration of 70 ng/ml in a DNA content. The mixture was preincubated at 85° C. for 10 min, and diluted 10-fold with the hybridization solution. This hybridization solution (about 40 µl) was added dropwise onto said air-dried sample on the slide glass. The slide glass was covered with a parafilm and heated at 95° C. for 2 min on a hotplate.

This slide glass was incubated at 37° C. for 16 hr in a moisture chamber, in which a paper towel moistened with 50% formamide solution was set, to allow the air-dried sample to hybridize with the labeled PCR amplification product.

After hybridization, the parafilm was removed from the slide glass in 5×SSC solution (40° C.), and the slide glass was heated in 2×SSC and 50% formamide at 40° C. for 30 min. Then, the slide glass was washed with TNE solution, and reacted with 5 µg/ml RNase in TNE solution for 10 min. The slide glass was washed successively with 2×SSC at 40° C. for 20 min (once), and with 0.2×SSC at 40° C. for 20 min (twice). The slide was immersed in 0.2×SSC solution (pH 8.5) containing 0.1 mM europium chloride, and the tissue section on the slide glass was observed with a fluorescence microscope.

As a result, a mosaic staining pattern was detected in liver cells in the lobulus on the slide glass. As a comparative example, hybridization was tried using FITC in the place of the labeled compound mentioned above. However, the fluorescence of FITC was significantly degraded when an FITC-labeled PCR product was obtained, so that the subsequent hybridization step could not be performed.

Thus, as an alternative, a DNA product was obtained by amplification using unlabeled oligonucleotides having the nucleotide sequences depicted in SEQ ID: NO: 1 and SEQ ID: NO: 2 as a pair of primers and a nucleic acid fraction derived from an HBsAg strongly positive patient-deived serum as a template. Said amplification product was reacted with FITC to give a fluorescence-labeled probe, which was subjected to hybridization, wherein no europium chloride was added. Hybridiztion using said FITC-labeled probe gave very weak signals, which showed that the FITC-labeled prove was obviously inferior to the labeled probe of the present invention.

EXAMPLE 5
Analysis of human pancreas tissue using labled human insulin

A labeled human insulin was preared using a standard human insulin (Sigma) in the same manner as in Exarnple 1.

A pancreas tissue excised from a human was treated in the same manner as in Example 2 to give a section. This section was placed on a slide glass and immersed in 4% formamide solution at room temperature for 10 min. To this section was added TBS solution [Tris-NaCl buffer (pH 7.6), 50 µl] containing 5% skim milk. The section was heated at 37° C. for 2 hr, and washed with TBS solution (pH 7.6) 3 times.

As a hybridization solution, a solution of 1 mM EDTA and 0.2% BSA in TBS solution (pH 7.6) was prepared.

The labeled human insulin was dissolved in this hybridization solution to the concentration of 10 ng/ml, and the mixture (about 40 µl) was dropped onto the pancreas tissue section. The slide glass was covered with parafilm, and incubated at 37° C. for 8 hr in a moisture chamber in which a paper towel moistened with 50% formamide solution was set, to allow the section to hybridize with the labeled probe.

After hybridization, the parafilm was removed from the slide glass in 5×SSC solution (40° C.), and the slide glass was heated in 2×SSC and 50% formamide at 40° C. for 30 min. Then, the slide glass was washed with TNE solution, and reacted with 5 µg/ml RNase in TNE solution for 10 min. The slide glass was washed successlvely with 2×SSC at 40° C. for 20 min (once), and with 0.2×SSC at 40° C. for 20 min (twice). The slide glass was immersed in 0.2×SSC solution (pH 8.5) containing 0.1 mM europium chloride, and the tissue section on the slide glss was observed with a fluorscence microscope.

As a result, signals derived from the fluorescent complex of the labeled human insulin and europium chloride were detected on the tissue section.

When hybridization was performed using an anti-human insulin receptor antibody (Austral Biologicals (ABI)) labeled with rhodamine in the place of the labeled human insulin mentioned above as a comparative example, almost the same level of fluorescence image was obtained.

Accordingly, it was conduded that the laeled human insulin of the invention specifically reacted with a human insulin receptor.

EXAMPLE 6
Analysis of chromosome preparation derived from peripheral blood cell using denatured DNA probe
(Culture of peripheral lymphocyte)

Sterilely obtained peripheral blood supplemented with heparin (1 ml) and RPMI1640 medium (GIBCO BRL, 9 ml) supplemented with 15% fetal calf serum were mixed, and transferred into a culture flask. Phytohemagglutinin (Welcome) was added to the final concentration of 10 g/ml, and the peripheral blood was cultured in a $CO_2$ incubator with 5% $CO_2$ atmosphere at 37° C. After 48 hrs of culture, thymidine (Sigma) was added to the final concentration of 300 µg/ml, and the culture was continued. At 63 hr after the start of the culture, peripheral blood cells comprising lymphocytes were tansferred to a new tube, and centrifuged at 1,200 rpm for 5 min. The cells were rinsed by adding RPMI1640 medium (10 ml) to the tube and gently stirring. Said rinising step was repeated once. RPMI1640 medium supplemented with 15% fetal calf serum (10 ml) and the peripheral blood cells comprising lymphocytes were mixed, and cultued. At 63.5 hr after the start of the culture, bromodxyuridine (Sigma) was added to the final concentration of 50 ng/ml, the mixture was stirred, and the culture was continued. At 70 hr after the start of the culture, the peripheral blood cells comprising lymphocytes were harvested by centrifugation at 1,200 rpm.
(Preparation of chromosome)

To the harvested peripheral blood cells was added 0.075 M KCl (10 ml), and the suspension was stood at room temperature for 30 min. After hypotonization, the suspension was centrifuged at 1,200 rpm for 5 min. The supematant (about 3 ml) and the precipitate were sufficiently stirred using a Pasteur pipette, and gradually dropped into methanol:acetic acid (3:1, carnoy solution, 10 ml). The mixture was sufficiently stirred, stood for 10 min and centrifuged at 1,200 rpm for 5 min. The supernatant was removed. To the precipitate was added a fresh carnoy solution (10 ml), and the both were mixed with stirring. This step of washing with carnoy solution was repeated twice. The concentration of the suspension was adjusted with caroy solution. The suspension was dropped onto the center of a slide glass, which was followed by steam fixation using a pot containing boiled water.

The fixed sample on the slide glass was dried at 37° C. overnight, which was followed by adhesion in a dry heat sterilizer at 65° C. for 4 hr to give a chromosome preparation. This chromosome preparation was stained with 2×SSC containing 1 μg/ml fluorescent dye, Hoechst 33258 (Molecular probe) for 5 min, gently rinsed with 2×SSC and covered with a cover glass, which was followed by standing on a hot plate (75° C.) for 3 min. The preparation was exposed to UV light on the hot plate at a distance of 1 cm from the preparation with a black light (20 W, Toshiba). The cover glass on the slide glass was removed and the slide glass was rinsed twice with distilled water, dried and stored at −20° C. with the chromosome preparation carried thereon.
(Preparation of labeled dUTP)

A labeled dUTP was prepared using dUTP (deoxy UTP, Toyo Boseki) in the same manner as in Example 1.

This labeled dUTP and KRAS ONCOGENE (Lab Logics, large probe) were subjected to nick translation method to give a labeled nucleic acid.

The nick translation followed the protocol using a nick translation kit manufactured by Boehringer. The labeled dUTP was used at a final concentration of 0.05 mM.

After the nick translation, 4 M ammonium acetate (2.5 μl), 10 mg/ml salmon sperm DNA (Sigma, 2.0 μl), 10 mg/ml E. coli tRNA (Sigma, 2.0 μl) and special grade ethanol (75 μl) were added to the nick translation reaction mixture (20 μl), admixed well, stored at −80° C. for 1 hr. and centrifuged at 15,000 rpm to give precipitate, which was stirred in special grade formamide to dissolution.
(hybridization)

To the labeled nucleic acid (5 μl) prepared according to the above-mentioned method was added 10 mg/ml Cot-1 DNA (manufaetured by Vysis, 5 μl) and incubated in a heat block at 70° C. for 10 min to denature the labeled probe to give a denatured DNA probe, which was quickly cooled in ice water.

Then, the above-mentioned slide glass carrying the chromosome preparation was immersed in a coupling jar filled with 70% formamide (2×SSC) at 70° C. to denature the sample with heat. The sample was immediately moved into 70% ethanol at −20° C., rapidly cooled for 2 min, dehydrated with 100% ethanol and dried. The above-mentioned denatured DNA probe was mixed in a solution having a final concentration of 50% formamide and 10% dexran sulfate (in 2×SSC) and placed on the above-mentioned chromosome preparation. The denatured DNA probe solution was uniformly spread thereon using a parafilm strip to prevent inclusion of air foams. The chromosome sample on the side glass and the denatured DNA probe were hybridized in a sealed moistened chamber containing a filter paper impregnated with 2×SSC on the bottom therein at 37° C. for 18 hr.

The parafilm was stripped off the slide glass and the slide glass was immersed in a coupling jar filled with 50% formide (in 2×SSC) at 37° C. and rinsed for 15 min. This slide glass was stood still in 2×SSC (room temperature) for 1 min and then stood still for 15 min in 1×SSC (room temperature) and 5 min in 4×SSC (room temperature). Then, 2×SSC (pH 8.5) containing 0.1 mM europium chloride was dropped on a slide glass and the tissue section strip on the slide giass was observed with a fluorescence microscope.

As a result, the 11th chromosome was found to have fluorescence, which coincided with the localization of nucleic acid contaning KRAS ONCOGENE, thereby confirming possible specific detection.

EXAMPLE 7

(Preparation of fluorescence-labeled streptoavidin)

Recombinant streptoavidin (24 mg, Boehringer Mannheim) was dissolved in 100 mM carbonate buffer (pH 9.3, 2 ml) and dialyzed against the same buffer. From the absorbance of dialysis solution at 280 nm, it was conformed to have a 3.4 mg/ml protein concentration. To the entire amount of 2 ml thereof was dropwise added an anhydrous DMF solution (0.4 ml) containing the labeled compound (7.4 mg) of Reference example 3 and the mixture was stirred at 25° C. for 1 hr. After stirring, the reaction mixture was eluted with 50 mM ammonium carbonate using Sephadex G-50 column (about 30 ml bed) to separate a non-reacted labeled compound. From the absorption coefficient 3.41× $10^4$ $(cm^{-1}M^{-1})$ at 330 nm of the protein fraction and the molecular weight of recombinant streptoavidin of about 52,000, the cross-linked labeled compound was calculated to be about 20 molecules per 1 molecule of streptoavidin. Sodium azide was added to the protein fraction to the concentration of 0.1%, adjusted to pH 6.5 with 1N HCl and stored at 4° C.

(Preparation of DNA probe using nick translation kit)

Using the KRAS ONCOGENE (Lab Logics, large probe) used in Example 6 and biotin-21-dUTP nick translation kit (Clontech), and following the protocol attached to the kit, biotin-21-dUTP was incorporated into the nucleic acid KRAS ONCOGENE to give a biotinylated KRAS ONCOGENE DNA probe. The biotin-21-dUTP has the following structure including a linkage group.

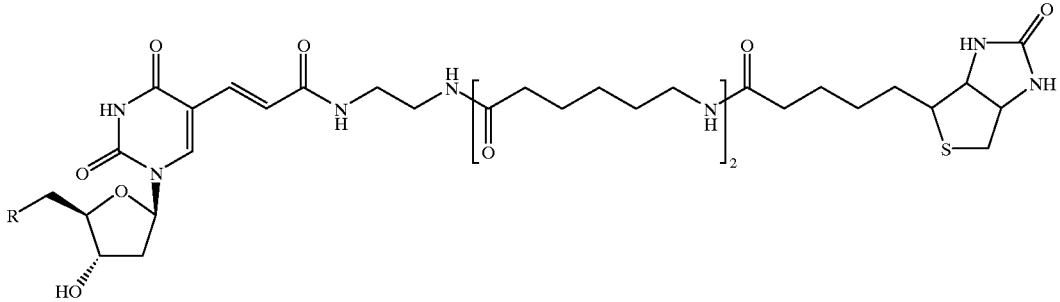

wherein R has the formula

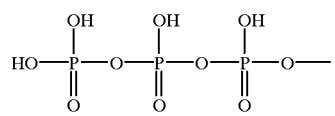

To the reaction mixture (20 μl) after nick translation reaction were added 4 M ammonium acetate (2.5 μl), 10 mg/ml salmon sperm DNA (Sigma, 2.0 μl), 10 mg/ml E. coli tRNA (Sigama, 2.0μl) and special grade ethanol (75 μl) and admixed well. After storing at −80° C. for 1 hr, it was centrifuged at 15,000 rpm and the precpitate was thoroughly stirred in special grade formamide to dissolution. (hybridization)

Completely in the same manner as in Example 6, a denatured DNA probe was prepared and hybridized with a chromosome preparation.

After hybridization, a parfilm was stripped off the slide glass and the slide glass was immersed in a couplingjar filled with 50% formamide (in 2×SSC) at 37° C. and rinsed for 15 min. This slide glass was stood still in 2×SSC (room temperature) for 1 min and then stood still for 15 min in 1×SSC (room temperature) and 5 min in 4×SSC (room temperature). The labeled streptoavidin prepared above was diluted with 2×SSC to the concentration of 0.02 mg/ml. The slide glass was left standing still in the solution at room temperature for 15 min. Using 1×SSC (room temperature), the slide glass was left standing still for 5 min, which step was repeated three times. Then, 2×SSC (pH 8.5) containing 0.1 mM europium chloride was dropped on a slide glass and the tissue section strip on the slide glass was observed with a fluorescence microscope.

As a result, the 11th chromosome was found to have fluorescence like Example 6, but apparently had stronger fluorescence. This fluorescence intensity was considered to reflect the high incorporation rate of biotinylated-21-UTP into the nucleic acid and the great number of the labeled compounds bonded to streptoavidin. The synchronized localization with KRAS ONCOGENE was confirmed and the method was concluded to be a specific detection method.

This application is based on patent application Nos. 119768/1998 and 184852/1998 filed in Japan, the contents of which are hereby incorporated by reference.

What is claimed is:

1. A method for analyzing an objective substance, comprising reacting a labeled probe with an objective substance on a biological sample, said probe comprising a label substance of the formula (I):

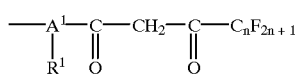

(I)

wherein $A^1$ is an aromatic group, $R^1$ is a hydrogen or $-COCH_2COC_nF_{2n+1}$ and n is an integer of 1–6, or a label substance of the following formula (II):

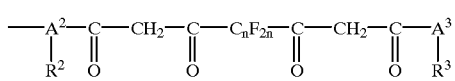

(II)

wherein $A^2$ and $A^3$ are the same or different and each is an aromatic group, $R^2$ and $R^3$ are the same or different and each is a hydrogen or $-COCH_2COC_nF_{2n+1}$ and n is an integer of 1–6, bonded to a probe selected from the group consisting of nucleic acid, nucleic acid binding protein, low molecular ligand and receptor for ligand (except antibody) via a cross-linking group or a cross-linking group and a conjugating group, adding a heavy metal ion and assaying fluorescence of the resultant fluorescent complex, and wherein the biological sample is a member selected from the group consisting of a tissue, a cell and a chromosome.

2. The analysis method of claim 1, wherein the objective substance is a member selected from the group consisting of a nucleic acid, a nucleic acid-bound protein, a low molecular weight ligand and a ligand receptor.

3. The analysis method of claim 1, wherein the crosslinking group is a sulfonyl group or a carbonyl group.

4. The anaylsis method of claim 1, wherein the conjugating group binds a cross-linking group and a probe.

5. The analysis method of claim 1, wherin the conjugating group is a divalent aliphatic hydrocarbon having 5 to 25 carbon atoms and having 0 to 7 amide bonds between carbons.

6. The analysis method of claim 1, wherin the conjugating group comprises an affinty-bound biotin and avidin.

7. The analysis method of claim 6, wherein the biotin is amide-bound with a divalent aliphatic hydrocarbon having 5 to 25 carbon atoms and having 0 to 7 amide bonds between carbons.

8. The analysis method of claim 7, wherein the aliphatic hydrocarbon is $-CH=CH-CO-NH-CH_2-CH_2-NH-(CO-CH_2-CH_2-CH_2-CH_2-CH_2-NH)_2-$ which is bonded to a probe.

9. A method for analyzing an objective substance comprsing reactng the ojective substance with a nucleic acid probe comprising a nucleotide to which biotin is bonded via a linkage group as a component on a biological sample and then with the label substance of the formula (I):

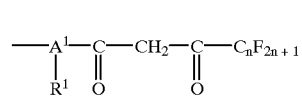

(I)

wherein $A^1$ is an aromatic group, $R^1$ is a hydrogen or $-COCH_2COC_nF_{2n+1}$ and n is an integer of 1–6, or a label substance of the following formula (II):

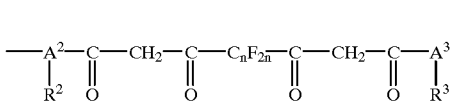

(II)

wherein $A^2$ and $A^3$ are the same or different and each is an aromatic group, $R^2$ and $R^3$ are the same or different and each is a hydrogen or $-COCH_2COC_nF_{2n+1}$ and n is an integer of 1–6, to which avidin is covalently bonded via a cross-linking group, adding a heavy metal ion and assaying fluoresence of the resultant flourescent complex, and wherein the biological sample is a member selected from the group consisting of a tissue, a cell, and a chromosome.

10. The method for analysis of claim 9, wherein the nucleic acid probe is obtained by reacting a nucleotide to which biotin is bonded via a linkage group, dNTPs and a single strand DNA in the presence of a primer and a DNA polymerase.

11. The method for analysis of claim 9, wherein the nucleic acid probe is obtained by reacting a nucleotide to which biotin is bonded via a linkage group, dNTPs and a double stranded DNA in the presence of 5'-exonuclease, DNase and a DNA polymerase.

12. The method for analysis of claim 9, wherein the linkage group is a divalent aliphatic hydrocabon having 5 to 25 carbon atoms and having 0 to 7 amide bonds between cabons.

13. The method for analysis of claim 9, wherein the aliphatic hydrocarbon is $-CH=CH-CO-NH-CH_2-CH_2-NH-(CO-CH_2-CH_2-CH_2-CH_2-CH_2-NH)_2-$.

14. The method for analysis of claim 9, wherein the cross-linking group is a sulfonyl group or carbonyl group.

15. The method for analysis of claim 9, wherein the nucleotide is dUTP.

16. A method for analyzing an objective substance, comprising adding a heavy metal ion to a labeled probe, said probe comprising a label substance of the formula (I):

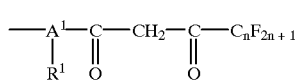

wherein $A^1$ is an aromatic group, $R^1$ is a hydrogen or —$COCH_2COC_nF_{2n+1}$ and n is an integer of 1–6, or a label substance of the following fornula (II):

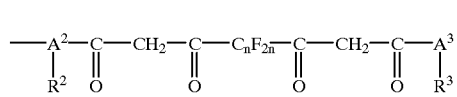

wherein $A^2$ and $A^3$ are the same or different and each is an aromatic group, $R^2$ and $R^3$ are the same or different and each is a hydrogen or —$COCH_2COC_nF_{2n+1}$ and n is an integer of 1–6, bonded to a probe seleted from the group consisting of nucleic acid, nucleic acid binding protein, low molecuar ligand and receptor for ligand (except antibody) to give a fluorescent complex, reacting the complex with an objective substance on a biological sample and assaying fluoresence of the resultant fluorescent complex, and wherein the biological sample is a member selected from the group consisting of a tissue, a cell and a chromosome.

17. The analysis method of claim 16, wherein the ojective substance is a member selected from the consisting of a nucleic acid, a nucleic acid-bound protein, a low molecular weight ligand and a ligand receptor.

18. The analysis method of claim 16, wherein the cross-linking group is a sulfonyl group or a carbonyl group.

19. The analysis method of claim 16, wherein the conjugating group binds a cross-linking group and a probe.

20. The analysis method of claim 16, wherein the conjugating group is a divalent aliphatic hydrocarbon having 5 to 25 carbon atoms and having 0 to 7 amide bonds between carbons.

21. The analysis method of claim 16, wherein the conjugaing group comprisis an affinity-bound biotin and avidin.

22. The analysis method of claim 21, wherein the biotin is amide-bound with a divalent aliphatic hydrocarbon having 5 to 25 carbon atoms and having 0 to 7 amide bonds between carbons.

23. The analysis method of claim 22, wherein the aliphatic hydrocarbon is —$CH{=}CH$—$CO$—$NH$—$CH_2$—$CH_2$—$NH$—$(CO$—$CH_2$—$CH_2$—$CH_2$—$CH_2$—$CH_2$—$NH)_2$— which is bonded to a probe.

* * * * *

UNITED STATES PATENT AND TRADEMARK OFFICE
CERTIFICATE OF CORRECTION

PATENT NO.    : 6,339,172 B1
DATED         : January 15, 2002
INVENTOR(S)   : Matsui et al.

It is certified that error appears in the above-identified patent and that said Letters Patent is hereby corrected as shown below:

<u>Title page,</u>
Item [54], please add "*in situ*" before the title.
Item [75], "2578-1-708, Noborito, Tama-ku, Kawasaki-shi, Kanagawa 214-0014" should read -- Kawasaki --.
Item [57], ABSTRACT,
Lines 1 and 3, "comprsing" should read as -- comprising --.

<u>Column 22,</u>
Lines 18-19, "comprsing" should read -- comprising --.
Line 57, "hydrocabon" should read -- hydrocarbon --.
Line 59, "cabons" should read -- carbons --.
Line 60, "claim 9" should read -- claim 12 --.

<u>Column 23,</u>
Line 23, "molecuar" should read -- molecular --.

<u>Column 24,</u>
Line 4, "the consisting" should read -- the group consisting --.
Lines 16-17, "conjugaing" should read -- conjugating --.

Signed and Sealed this

Twenty-fourth Day of September, 2002

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.   : 6,339,172 B1
DATED        : January 15, 2002
INVENTOR(S)  : Matsui et al.

It is certified that error appears in the above-identified patent and that said Letters Patent is hereby corrected as shown below:

Title page,
Item [54], please add "*in situ*" before the title.
Item [75], "2578-1-708, Noborito, Tama-ku, Kawasaki-shi, Kanagawa 214-0014" should read -- Kawasaki --.
Item [57], ABSTRACT,
Lines 1 and 3, "comprsing" should read as -- comprising --.

Column 22,
Lines 18-19, "comprsing" should read -- comprising --.
Line 57, "hydrocabon" should read -- hydrocarbon --.
Line 59, "cabons" should read -- carbons --.
Line 60, "claim 9" should read -- claim 12 --.

Column 23,
Line 23, "molecuar" should read -- molecular --.

Column 24,
Line 4, "the consisting" should read -- the group consisting --.
Lines 16-17, "conjugaing" should read -- conjugating --.

Signed and Sealed this

Fifteenth Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,339,172 B1  Page 1 of 1
DATED : January 15, 2002
INVENTOR(S) : Matsui et al.

It is certified that error appears in the above-identified patent and that said Letters Patent is hereby corrected as shown below:

Title page,
Item [73], "Kawasa" should read -- Kawasaki --.

Signed and Sealed this

Eleventh Day of March, 2003

JAMES E. ROGAN
*Director of the United States Patent and Trademark Office*